(12) United States Patent
Kim et al.

(10) Patent No.: US 8,759,561 B2
(45) Date of Patent: Jun. 24, 2014

(54) CATALYST, METHOD OF PREPARING THE SAME, AND METHOD OF PREPARING AROMATIC CARBONATE FROM DIALKYL CARBONATE USING THE SAME

(71) Applicant: Cheil Industries Inc., Kumi (KR)

(72) Inventors: Mie Ock Kim, Uiwang-si (KR); Chang Hoon Lee, Uiwang-si (KR); Dong Baek Kim, Uiwang-si (KR)

(73) Assignee: Cheil Industries Inc., Gumi-si (KR)

( * ) Notice: Subject to any disclaimer, the term of this patent is extended or adjusted under 35 U.S.C. 154(b) by 0 days.

(21) Appl. No.: 13/652,800

(22) Filed: Oct. 16, 2012

(65) Prior Publication Data
US 2013/0165681 A1 Jun. 27, 2013

(30) Foreign Application Priority Data
Dec. 27, 2011 (KR) ........................ 10-2011-0143775

(51) Int. Cl.
*C07F 7/22* (2006.01)
*C07C 68/06* (2006.01)

(52) U.S. Cl.
USPC .......................................... 556/83; 558/274

(58) Field of Classification Search
None
See application file for complete search history.

(56) References Cited

U.S. PATENT DOCUMENTS 5,463,102 A * 10/1995 Schon et al. ................. 558/274

FOREIGN PATENT DOCUMENTS

JP 2008163148 A * 7/2008

OTHER PUBLICATIONS

Machine translation of JP 2008163148 A.*

* cited by examiner

*Primary Examiner* — Brandon Fetterolf
*Assistant Examiner* — Ana Z Muresan
(74) *Attorney, Agent, or Firm* — Additon, Higgins, Pendleton & Ashe, P.A.

(57) ABSTRACT

The present invention provides a catalyst for synthesizing an aromatic carbonate, a method of preparing the same, and a method of preparing an aromatic carbonate from dialkyl carbonate using the catalyst. The catalyst has a unit structure consisting of Formulae 1a, 1b or 1c:

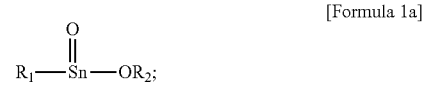

[Formula 1a]

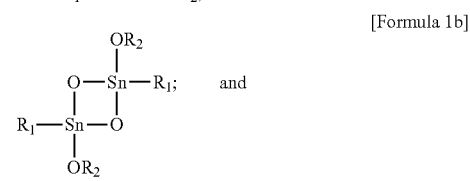

[Formula 1b]

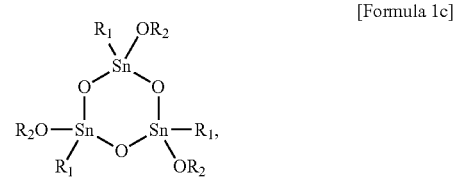

[Formula 1c]

wherein $R_1$ is C1-C5 alkyl, $R_2$ is substituted or unsubstituted phenyl.

7 Claims, 1 Drawing Sheet

CATALYST, METHOD OF PREPARING THE SAME, AND METHOD OF PREPARING AROMATIC CARBONATE FROM DIALKYL CARBONATE USING THE SAME

CROSS-REFERENCE TO RELATED APPLICATIONS

This application claims priority under 35 USC Section 119 to and the benefit of Korean Patent Application No. 10-2011-0143775 filed on Dec. 27, 2011, the entire disclosure of which is incorporated herein by reference.

FIELD OF THE INVENTION

The present invention relates to a catalyst, a method of preparing the same and a method of preparing an aromatic carbonate from dialkyl carbonate using the same.

BACKGROUND OF THE INVENTION

Aromatic carbonates are monomers useful for the preparation of polycarbonates and many studies have been conducted to develop preparation methods thereof. Conventionally, aromatic carbonate esters are prepared by phosgenation of phenol and phosgene in the presence of an alkali. However, this method uses poisonous phosgene and a neutral salt generated as a by-product must be treated.

Accordingly, various attempts have been made to develop a method of preparing an aromatic carbonate ester without phosgene. For example, a method of preparing an aromatic carbonate ester through oxidative carbonylation of an aromatic alcohol with carbon monoxide is known. This method is disadvantageous in that reaction rate and yield are low irrespective of the use of organic metal compounds such as palladium, manganese, cobalt and the like as catalysts; in that there is a risk of explosion due to the use of gas mixture of carbon monoxide and oxygen; and in that the method uses noxious carbon monoxide.

In order to solve such disadvantages, transesterification of phenol and an aliphatic carbonate ester such as dimethyl carbonate to produce an aromatic carbonate ester has been developed. Transesterification is generally conducted in the presence of a catalyst, for example, PbO, $TiX_4$ (X=alkoxy or aryloxy group), $SnR_2(OPh)_2$ (R=alkyl group), and the like. However, PbO has high stability but low catalytic activity, causing a significantly low reaction rate. $TiX_4$ and $SnR_2(OPh)_2$ have a higher activity than PbO, but have inadequate activity and generate a substantial amount of ether as by-products.

Therefore, there is a need for a method of preparing aromatic carbonate in high yield at low reaction temperature using dialkyl carbonate as a starting material instead of carbon monoxide.

SUMMARY OF THE INVENTION

The present invention provides a method of preparing an aromatic carbonate. The method can result in a high yield at low reaction temperature within a short period of time using dialkyl carbonate as a reactant instead of carbon monoxide. The method can provide high catalytic activity and selectivity to accelerate esterification of dialkyl carbonate while reducing by-production of ethers as compared with catalysts in the related art, thereby enabling effective preparation of diaryl carbonate.

The present invention also provides a catalyst for synthesizing an aromatic carbonate. The catalyst has a unit structure of Formula 1:

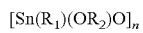 [Formula 1]

wherein:

$R_1$ is C1-C5 alkyl, $R_2$ is substituted or unsubstituted phenyl, and n is an integer from 1 to 10.

In one embodiment, $R_1$ may be methyl, ethyl, propyl or butyl, and $R_2$ may be phenyl.

In exemplary embodiments, the catalyst may include an organic tin compound represented by Formulae 1a to 1c or a combination thereof:

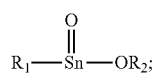 [Formula 1a]

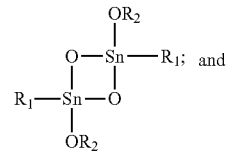 [Formula 1b]

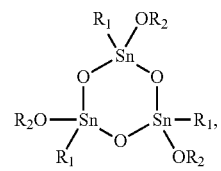 [Formula 1c]

wherein $R_1$ and $R_2$ are the same as defined in Formula 1.

The present invention also provides a method of preparing the catalyst for synthesizing an aromatic carbonate. In one embodiment, the method may include reacting a catalyst precursor represented by Formula 2 with $R_2OH$ wherein $R_2$ is substituted or unsubstituted phenyl.

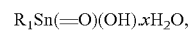 [Formula 2]

wherein $R_1$ is C1-C5 alkyl and x ranges from 0 to 5.

The method may further include removing unreacted $R_2OH$ from the reactant.

The present invention further provides a method of preparing an aromatic carbonate from dialkyl carbonate. In one embodiment, the method may include reacting an aromatic hydroxyl compound with dialkyl carbonate in the presence of the catalyst for synthesizing aromatic carbonate.

In one embodiment, the catalyst may be used in an amount of about $1.0 \times 10^{-5}$ mole to about $1.0 \times 10^{-2}$ mole based on about 1 mole of the dialkyl carbonate.

The reaction may be carried out at a temperature from about 150° C. to about 280° C.

The aromatic hydroxyl compound may be represented by Formula 3:

 [Formula 3]

wherein Ar is substituted or unsubstituted aryl.

The dialkyl carbonate may be represented by Formula 4:

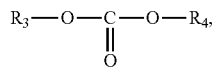
[Formula 4]

wherein $R_3$ and $R_4$ are the same or different and are each independently C1-C6 alkyl.

In another embodiment, the method of preparing an aromatic carbonate from dialkyl carbonate includes: reacting a catalyst precursor represented by Formula 2 with $R_2OH$ (wherein $R_2$ is substituted or unsubstituted phenyl) to form a reactant; and introducing dialkyl carbonate to the reactant to react the dialkyl carbonate with an aromatic hydroxyl compound (such as residual $R_2OH$ from the first step) to form the aromatic carbonate.

$$R_1Sn(=O)(OH)\cdot xH_2O, \qquad \text{[Formula 2]}$$

wherein $R_1$ is C1-C5 alkyl, and x ranges from 0 to 5.

DETAILED DESCRIPTION OF THE INVENTION

Figure 1:
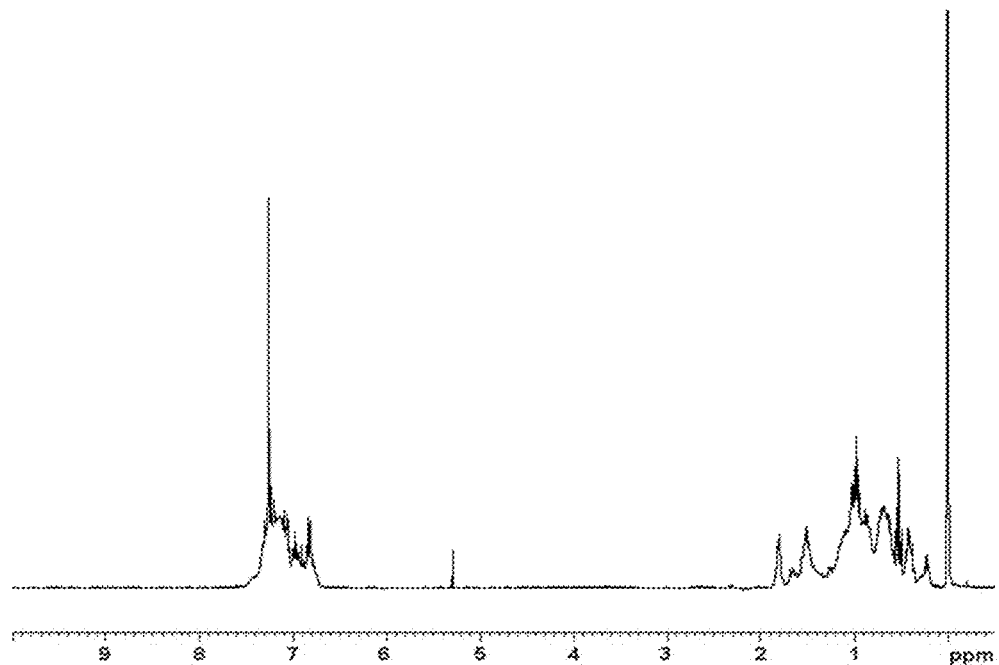
FIG. 1 is NMR data of a catalyst prepared in Preparation Example 1 of the present application.
Figure 2:
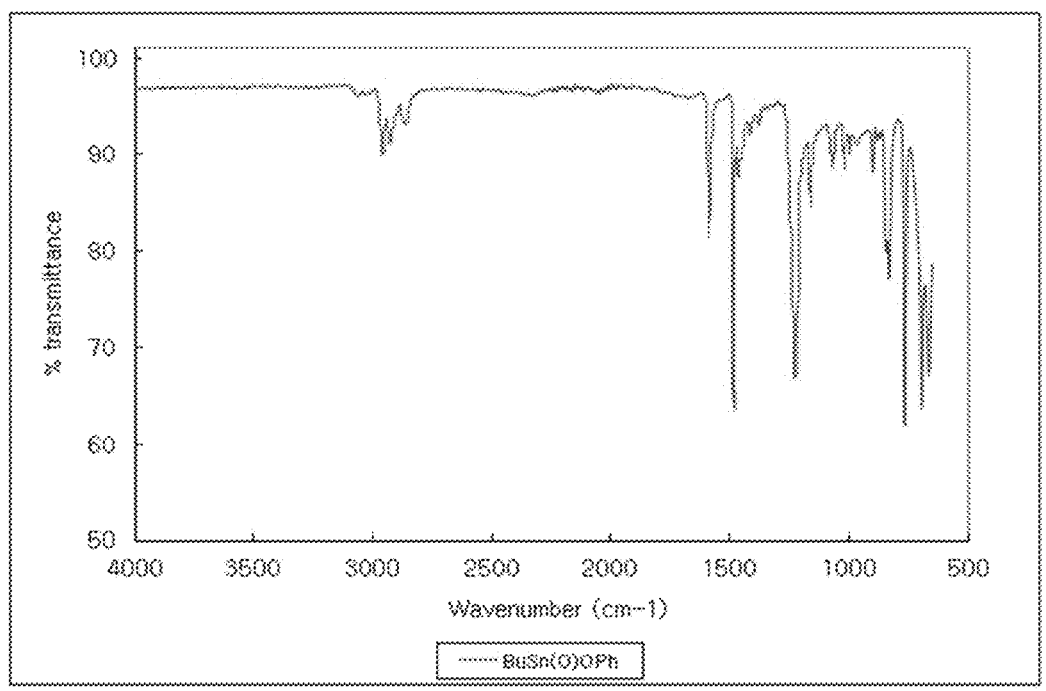
FIG. 2 is an IR spectrum of the catalyst prepared in Preparation Example 1 of the present application.

The present invention now will be described more fully hereinafter in the following detailed description of the invention, in which some, but not all embodiments of the invention are described. Indeed, this invention may be embodied in many different forms and should not be construed as limited to the embodiments set forth herein; rather, these embodiments are provided so that this disclosure will satisfy applicable legal requirements.

The present invention provides an organic tin compound catalyst having a unit structure of Formula 1:

$$[Sn(R_1)(OR_2)O]_n \qquad \text{[Formula 1]}$$

wherein:

$R_1$ is C1-C5 alkyl, $R_2$ is substituted or unsubstituted phenyl, and n is an integer from 1 to 10.

In Formula 1, $R_1$ can be methyl, ethyl, propyl or butyl, for example butyl, and $R_2$ can be phenyl. In Formula 1, n can be an integer from 1 to 5. Examples of substituents that can be used in the substitution of the phenyl include without limitation C1-C4 alkyl, halogen, C1 to C10 alkoxy, a nitro group, a cyano group, and the like, and combinations thereof.

In some embodiments, the organic tin compound catalysts having the unit structure of Formula 1 may include organic tin compounds represented by Formulae 1a to 1c, and these compounds may be used alone or in combination thereof:

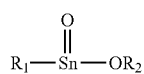
[Formula 1a]

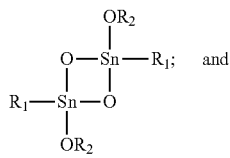
[Formula 1b]

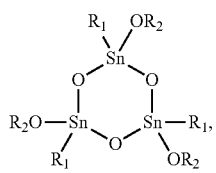
[Formula 1c]

wherein $R_1$ and $R_2$ are the same as defined in Formula 1.

The organic tin compound catalyst having the unit structure of Formula 1 may be prepared by reacting a catalyst precursor represented by Formula 2 with $R_2OH$ wherein $R_2$ is substituted or unsubstituted phenyl as defined above.

$$R_1Sn(=O)(OH)\cdot xH_2O, \qquad \text{[Formula 2]}$$

wherein $R_1$ is C1-C5 alkyl and x ranges from 0 to 5.

The molar ratio of the catalyst precursor of Formula 2 to $R_2OH$ ranges from about 1:1 to about 1:100, for example from about 1:1 to about 1:10, and as another example from about 1:1 to about 1:3. When the molar ratio of the catalyst precursor of Formula 2 to $R_2OH$ is within this range, the resulting catalyst can be easily recovered from the reactant.

Although there is no limitation as to temperature, this reaction can be carried out at a temperature of about 100° C. to about 180° C. Further, in this reaction, unreacted $R_2OH$ or low boiling point materials can be removed by a typical manner when starting the reaction or after completing the reaction.

After the reaction, the resulting product may be introduced into the aromatic carbonate preparation process without separating the organic tin compound catalyst having the unit structure of Formula 1, or may be introduced into the aromatic carbonate preparation process after separating only the organic tin compound catalyst having the unit structure of Formula 1 and purifying the organic tin compound.

In exemplary embodiments, the resulting product may be introduced into the aromatic carbonate preparation process after removing the unreacted $R_2OH$.

In one embodiment, the method of preparing the aromatic carbonate may include reacting an aromatic hydroxyl compound with dialkyl carbonate in the presence of the organic tin compound having the unit structure of Formula 1.

In another embodiment, the method includes reacting a catalyst precursor represented by Formula 2 with $R_2OH$ wherein $R_2$ is substituted or unsubstituted phenyl to form a reactant, and introducing dialkyl carbonate to the reactant to react the dialkyl carbonate with an aromatic hydroxyl compound (such as residual $R_2OH$ from the first step) to form the aromatic carbonate. In this case, the dialkyl carbonate may be optionally introduced together with additional $R_2OH$, wherein $R_2$ is substituted or unsubstituted phenyl.

In another embodiment, the organic tin compound catalyst having the unit structure of Formula 1 may be used in an amount of about $1.0\times10^{-5}$ to about $1.0\times10^{-2}$ mole, for example about $3.0\times10^{-5}$ to about $1.0\times10^{-4}$ mole, based on about 1 mole of the dialkyl carbonate. When the organic tin compound catalyst is used in an amount within this range, good catalytic effect can be obtained together with a high recovery rate of the catalyst.

The aromatic hydroxyl compound may be represented by Formula 3:

Ar—OH,  [Formula 3]

wherein Ar is substituted or unsubstituted aryl.

In Formula 3, Ar can be a phenyl group or a naphthyl group. Examples of substituents that can be used in the substitution of the aryl group include without limitation C1-C4 alkyl, halogen, C1 to C10 alkoxy, a nitro group, a cyano group, and the like, and combinations thereof.

Examples of the aromatic hydroxyl compound include without limitation phenol, naphthol, cresol, chlorophenol, alkylphenol, alkoxyphenol, nitrophenol, cyanophenol, and the like, and combinations thereof. In exemplary embodiments, phenol may be used as the aromatic hydroxyl compound.

The dialkyl carbonate may be represented by Formula 4:

$$R_3-O-\underset{\underset{O}{\|}}{C}-O-R_4,$$  [Formula 4]

wherein $R_3$ and $R_4$ are the same or different and are each independently C1-C6 alkyl. In exemplary embodiments, $R_3$ and $R_4$ are each independently methyl, ethyl group, propyl, or butyl.

Examples of the dialkyl carbonate include without limitation dimethylcarbonate, diethylcarbonate, dipropylcarbonate, dibutylcarbonate, methylethylcarbonate, methylpropylcarbonate, ethylpropylcarbonate, and the like, and combinations thereof. In exemplary embodiments, dimethylcarbonate may be used as the dialkyl carbonate.

In one embodiment, the reaction can be carried out at a temperature ranging from about 150° C. to about 280° C., for example from about 180° C. to about 250° C., and as another example from about 200° C. to about 230° C. When the reaction temperature is within this range, diarylcarbonate can be produced in high yield.

In this embodiment, transesterification may be carried out at a pressure from about 0.1 bar to about 6 bar. In exemplary embodiments, the transesterification can be carried at a pressure from about 1 bar to about 6 bar.

Although the reaction time is not specifically limited, the reaction may be carried out for about 1 second to about 60 minutes.

The molar ratio of dialkyl carbonate to phenol can be from about 1:2 to about 1:3, but is not limited thereto.

Next, the constitution and functions of the present invention will be explained in more detail with reference to the following examples. It should be understood that these examples are provided for illustrative purposes only and are not to be in any way construed as limiting the present invention. A description of details apparent to those skilled in the art will be omitted herein.

EXAMPLES

Preparation Example 1

Preparation of Catalyst A

In a 100 ml glass flask equipped with a cooling reflux column, BuSn(=O)(OH).xH$_2$O (5 g, 22.961 mmol) and phenol (32.41 g, 344.38 mmol) are placed, and heated to 120° C. After stirring the compounds at 120° C. for 6 hours, the unreacted phenol and resulting low boiling point materials are removed from the flask through distillation. A white crystalline solid (Catalyst A) is obtained by cooling the resultant. The obtained solid is subjected to NMR, IR and EA analysis to confirm the structure of $[Sn(Bu)(OPh)O]_n$ (n=1~12). The results are provided in Tables 1 and 2.

Preparation Example 2

Preparation of Catalyst B

In a 200 ml autoclave reactor equipped with an outer heater and having an inner volume of 200 ml, phenol (0.09 g, 1 mmol) and BuSn(=O)(OH).xH$_2$O (0.0048 g, 0.022 mmol) are placed, followed by introducing nitrogen into the reactor to displace oxygen, heating the reactor to 150° C. and stirring the compounds for 1 hour. Then, the produced low boiling point materials are removed through a vent at 110° C. for 5 minutes and the reactor is cooled below 50° C. using a cooler to obtain a catalyst mixture (Catalyst B).

Example 1

In a 200 ml autoclave reactor equipped with an outer heater and having an inner volume of 200 ml, phenol (65.88 g, 700 mmol), dimethyl carbonate (31.53 g, 350 mmol) and Catalyst A (0.0063 g, 0.022 mmol based on Sn) prepared in Preparation Example 1 are placed, followed by introducing nitrogen into the reactor to displace oxygen, and heating the reactor while stirring the reactor. After the reactor is heated to 230° C., the reactor is left for 15 minutes and then cooled using a cooler to prepare diphenyl carbonate. The composition of the product is analyzed by gas chromatography to determine conversion rate and selectivity. The results are provided in Table 1.

Example 2

Diphenyl carbonate is prepared by the same method as in Example 1 except that Catalyst B prepared in Preparation Example 2 is used. The composition of the product is analyzed by gas chromatography to determine conversion rate and selectivity. The results are provided in Table 1.

Example 3

In a 200 ml autoclave reactor equipped with an outer heater and having an inner volume of 200 ml, phenol (65.88 g, 700 mmol) and BuSn(=O)(OH).xH$_2$O (0.0048 g, 0.022 mmol based on Sn) are placed, followed by introducing nitrogen into the reactor to displace oxygen, heating the reactor to 150° C. and stirring the compounds for 1 hour. Then, the produced low boiling point materials are removed from the reactor through a vent at 110° C. for 5 minutes and the reactant is cooled below 50° C. using a cooler. Then, dimethyl carbonate (31.53 g, 350 mmol) is added to the reactor, followed by introducing nitrogen into the reactor to displace oxygen therein, and heating the reactor while stirring the reactor. After the reactor is heated to 230° C., the reactor is left for 15 minutes and then cooled using a cooler to prepare diphenyl carbonate. The composition of the product is analyzed by gas chromatography to determine conversion rate and selectivity. The results are provided in Table 2.

Example 4

Diphenyl carbonate is prepared by the same method as in the Example 3 except that the reactor is heated to 230° C. and

Example 5

Diphenyl carbonate is prepared by the same method as in the Example 3 except that BuSn(=O)(OH).xH$_2$O (0.0089 g, 0.041 mmol based on Sn) is used. The composition of the product is analyzed by gas chromatography to determine conversion rate and selectivity. The results are provided in Table 2.

Example 6

Diphenyl carbonate is prepared by the same method as in the Example 3 except that BuSn(=O)(OH).xH$_2$O (0.0179 g, 0.082 mmol based on Sn) is used. The composition of the product is analyzed by gas chromatography to determine conversion rate and selectivity. The results are provided in Table 2.

Example 7

Diphenyl carbonate is prepared by the same method as in the Example 3 except that BuSn(=O)(OH).xH$_2$O (0.0357 g, 0.164 mmol based on Sn) is used. The composition of the product is analyzed by gas chromatography to determine conversion rate and selectivity. The results are provided in Table 2.

Example 8

Diphenyl carbonate is prepared by the same method as in the Example 3 except that the reactor is heated to 220° C. and left for 15 minutes, instead of being heated to 230° C. and left for 15 minutes. The composition of the product is analyzed by gas chromatography to determine conversion rate and selectivity. The results are provided in Table 2.

Example 9

In a 200 ml autoclave reactor having an inner volume of 200 ml and equipped with an outer heater and a column filled with 4A Molecular Sieve and having a diameter of 2.54 cm and a length of 15 cm, phenol (65.88 g, 700 mmol), dimethyl carbonate (31.53 g, 350 mmol) and BuSn(=O)(OH) (0.0048 g, 0.022 mmol based on Sn) are placed, followed by introducing nitrogen into the reactor to displace oxygen therein, and heating the reactor while stirring the reactor. After the reactor is heated to 230° C., the reactor was left for 30 minutes and cooled using a cooler to prepare diphenyl carbonate. The composition of the product is analyzed by gas chromatography to determine the conversion rate and selectivity. The results are provided in Table 3.

Example 10

Diphenyl carbonate is prepared by the same method as in the Example 9 except that the reactor is heated to 230° C. and left for 60 minutes instead of being heated to 230° C. and left for 30 minutes. The composition of the product is analyzed by gas chromatography to determine conversion rate and selectivity. The results are provided in Table 3.

Example 11

Diphenyl carbonate is prepared by the same method as in the Example 9 except that the reactor is heated to 230° C. and left for 120 minutes instead of being heated to 230° C. and left for 30 minutes. The composition of the product is analyzed by gas chromatography to determine conversion rate and selectivity. The results are provided in Table 3.

Comparative Example 1

Diphenyl carbonate is prepared by the same method as in the Example 1 except that Bu$_2$SnO is used as a catalyst instead of Catalyst A. The composition of the product is analyzed by gas chromatography to determine conversion rate and selectivity. The results are provided in Table 1.

Comparative Example 2

Diphenyl carbonate is prepared by the same method as in the Example 1 except that Ph$_2$SnO is used as a catalyst instead of Catalyst A. The composition of the product is analyzed by gas chromatography to determine conversion rate and selectivity. The results are provided in Table 1.

Comparative Example 3

Diphenyl carbonate is prepared by the same method as in the Example 1 except that Bu$_2$Sn(OAc)$_2$ is used as a catalyst instead of Catalyst A. The composition of the product is analyzed by gas chromatography to determine conversion rate and selectivity. The results are provided in Table 1.

Comparative Example 4

Diphenyl carbonate is prepared by the same method as in the Example 1 except that Bu$_2$Sn (maleate) is used as a catalyst instead of Catalyst A. The composition of the product is analyzed by gas chromatography to determine conversion rate and selectivity. The results are provided in Table 1.

Comparative Example 5

Diphenyl carbonate is prepared by the same method as in the Example 1 except that (OAc)Bu$_2$SnOSnBu$_2$(OAc) is used as a catalyst instead of Catalyst A. The composition of the product is analyzed by gas chromatography to determine conversion rate and selectivity. The results are provided in Table 1.

Comparative Example 6

Diphenyl carbonate is prepared by the same method as in the Example 1 except that PbO is used as a catalyst instead of Catalyst A. The composition of the product is analyzed by gas chromatography to determine conversion rate and selectivity. The results are provided in Table 1.

Comparative Example 7

Diphenyl carbonate is prepared by the same method as in the Example 1 except that the reactor is heated to 230° C. and left for 3 minutes instead of being heated to 230° C. and left for 15 minutes and PbO is used as a catalyst instead of Catalyst A. The composition of the product is analyzed by gas chromatography to determine conversion rate and selectivity. The results are provided in Table 1.

Comparative Example 8

In a 200 ml autoclave reactor having an inner volume of 200 ml and equipped with an outer heater and a column filled with 4A Molecular Sieve and having a diameter of 2.54 cm and a length of 15 cm, phenol (65.88 g, 700 mmol), dimethyl carbonate (31.53 g, 350 mmol) and PbO (0.0049 g, 0.022 mmol based on Pb) are placed, followed by introducing nitrogen into the reactor to displace oxygen therein, and heating the reactor while stirring the reactor. After the reactor is heated to 230° C., the reactor is left for 30 minutes and cooled using a cooler to prepare diphenyl carbonate. The composition of the product is analyzed by gas chromatography to determine conversion rate and selectivity. The results are provided in Table 3.

Table 3 shows the results of applying Molecular Sieve. As shown in Table 3, it can be seen that the use of the catalysts according to the present invention results in good conversion rate and selectivity even with a short reaction time.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation, the scope of the invention being defined in the claims.

What is claimed is:

1. A catalyst for synthesizing an aromatic carbonate having a unit structure consisting of Formulae 1a, 1b or 1c:

TABLE 1

| | Catalyst | Reaction Temp. (° C.) | Catalyst Amount (ppm) | Reaction Time (min) | DMC:PhOH (molar ratio) | Conversion Rate (%) | Selectivity (%) |
|---|---|---|---|---|---|---|---|
| Example 1 | [Sn(Bu)(OPh)O]$_n$ | 230 | 27 | 15 | 1:2 | 7.92 | 99.44 |
| Example 2 | [Sn(Bu)(OPh)O]$_n$ | 230 | 27 | 15 | 1:2 | 7.92 | 99.44 |
| Comparative Example 1 | Bu$_2$SnO | 230 | 27 | 15 | 1:2 | 1.58 | 93.04 |
| Comparative Example 2 | Ph$_2$SnO | 230 | 27 | 15 | 1:2 | 5.09 | 99.61 |
| Comparative Example 3 | Bu$_2$Sn(OAc)$_2$ | 230 | 27 | 15 | 1:2 | 2.46 | 96.34 |
| Comparative Example 4 | Bu$_2$Sn(maleate) | 230 | 27 | 15 | 1:2 | 1.48 | 93.92 |
| Comparative Example 5 | (OAc)Bu$_2$SnOSnBu$_2$(OAc) | 230 | 54 | 15 | 1:2 | 2.54 | 98.43 |
| Comparative Example 6 | PbO | 230 | 47 | 15 | 1:2 | 5.26 | 97.91 |
| Comparative Example 7 | PbO | 230 | 47 | 30 | 1:2 | 7.85 | 98.09 |

* The amount of catalyst is based on Sn or Pb.

As shown in Table 1, it can be seen that Examples 1 and 2 using the catalysts of the present invention demonstrate excellent conversion rate and selectivity at the same temperature and time, as compared to Comparative Examples 1 to 7.

The conversion rate and selectivity in accordance with temperature, catalyst amount, reaction time and molar ratio of DMC:PhOH are provided in Table 2.

TABLE 2

| | Catalyst | Reaction Temp. (° C.) | Sn Cat. Amount (ppm) | Reaction Time (min) | DMC:PhOH (molar ratio) | Conversion Rate (%) | Selectivity (%) |
|---|---|---|---|---|---|---|---|
| Example 3 | [Sn(Bu)(OPh)O]$_n$ | 230 | 27 | 10 | 1:2 | 7.59 | 98.42 |
| Example 4 | [Sn(Bu)(OPh)O]$_n$ | 230 | 27 | 5 | 1:2 | 6.81 | 98.41 |
| Example 5 | [Sn(Bu)(OPh)O]$_n$ | 230 | 50 | 5 | 1:2 | 7.06 | 99.61 |
| Example 6 | [Sn(Bu)(OPh)O]$_n$ | 230 | 100 | 5 | 1:2 | 7.19 | 99.26 |
| Example 7 | [Sn(Bu)(OPh)O]$_n$ | 230 | 200 | 5 | 1:2 | 7.07 | 99.21 |
| Example 8 | [Sn(Bu)(OPh)O]$_n$ | 220 | 27 | 15 | 1:2 | 6.45 | 99.67 |

* The amount of catalyst is based on Sn.

TABLE 3

| | Catalyst | Reaction Temp. (° C.) | Catalyst amount (ppm) | Reaction Time (min) | DMC:PhOH (molar ratio) | Conversion Rate (%) | Selectivity (%) |
|---|---|---|---|---|---|---|---|
| Example 9 | [Sn(Bu)(OPh)O]$_n$ | 230 | 27 | 30 | 1:2 | 14.15 | 99.37 |
| Example 10 | [Sn(Bu)(OPh)O]$_n$ | 230 | 27 | 60 | 1:2 | 17.92 | 98.99 |
| Example 11 | [Sn(Bu)(OPh)O]$_n$ | 230 | 27 | 120 | 1:2 | 17.13 | 98.86 |
| Comparative Example 8 | PbO | 230 | 47 | 30 | 1:2 | 4.50 | 97.57 |

* The amount of catalyst is based on Sn or Pb.

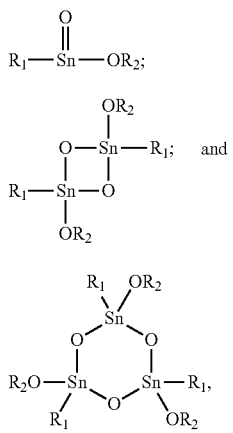

[Formula 1a]

[Formula 1b]

[Formula 1c]

wherein:

R₁ is C1-C5 alkyl,

R₂ is substituted or unsubstituted phenyl.

2. The catalyst according to claim 1, wherein $R_1$ is methyl, ethyl, propyl or butyl, and $R_2$ is phenyl.

3. A method of preparing an aromatic carbonate from dialkyl carbonate, comprising: reacting an aromatic hydroxyl compound with dialkyl carbonate in the presence of the catalyst according to claim 1.

4. The method according to claim 3, wherein the catalyst is used in an amount of about $1.0 \times 10^{-5}$ to about $1.0 \times 10^{-2}$ mole based on about 1 mole of the dialkyl carbonate.

5. The method according to claim 3, wherein the reaction is carried out at a temperature from about 150° C. to about 280° C.

6. The method according to claim 3, wherein the aromatic hydroxyl compound is represented by Formula 3:

Ar—OH, [Formula 3]

wherein Ar is substituted or unsubstituted aryl.

7. The method according to claim 3, wherein the dialkyl carbonate is represented by Formula 4:

[Formula 4]

wherein $R_3$ and $R_4$ are the same or different and are each independently C1-C6 alkyl.

* * * * *